(12) United States Patent
Gordon

(10) Patent No.: US 6,224,211 B1
(45) Date of Patent: May 1, 2001

(54) SUPER VISION

(75) Inventor: Eugene I. Gordon, Mountainside, NJ (US)

(73) Assignee: Medjet, Inc., Edison, NJ (US)

( * ) Notice: Subject to any disclaimer, the term of this patent is extended or adjusted under 35 U.S.C. 154(b) by 0 days.

(21) Appl. No.: 09/328,012

(22) Filed: Jun. 8, 1999

(51) Int. Cl.[7] ............................. G02C 7/02; A61B 17/22; A61N 5/06
(52) U.S. Cl. .................................. 351/177; 606/5
(58) Field of Search ............... 351/160 R, 160 H, 351/161–162, 176–177; 623/6, 11, 6.23–6.24; 606/4–5, 107

(56) References Cited

U.S. PATENT DOCUMENTS

| | | | | |
|---|---|---|---|---|
| 3,831,604 | * | 8/1974 | Neefe | 351/160 R |
| 4,195,919 | * | 4/1980 | Shelton | 351/160 R |
| 4,564,484 | * | 1/1986 | Neefe | 264/2.6 |
| 5,050,981 | * | 9/1991 | Roffman | 351/159 |
| 5,728,156 | * | 3/1998 | Gupta | 351/160 R |
| 5,969,790 | * | 10/1999 | Onufryk | 351/175 |
| 6,082,856 | * | 7/2000 | Dunn et al. | 351/160 H |

* cited by examiner

*Primary Examiner*—Scott J. Sugarman
*Assistant Examiner*—Jordan M. Schwartz

(57) ABSTRACT

Improvement of visual acuity beyond the "20—20" standard or achievement of "super acute vision" is effected by means of either selective refractive surgery or by use of a centering corneal contact lens which non-refractively corrects for natural spherical aberrations of the eye.

17 Claims, 2 Drawing Sheets

Figure 1A:
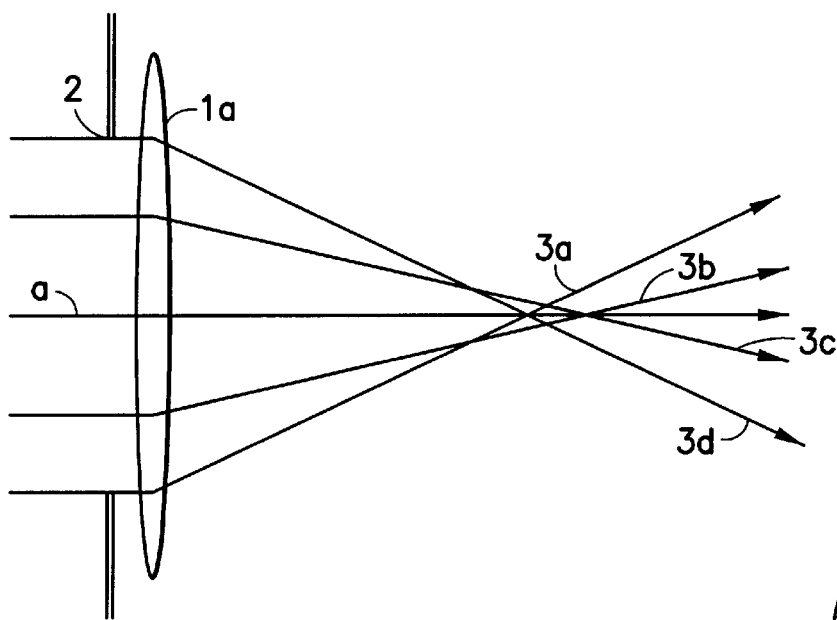
Figure 1A:
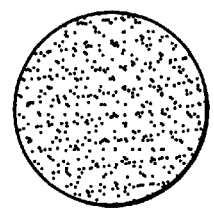

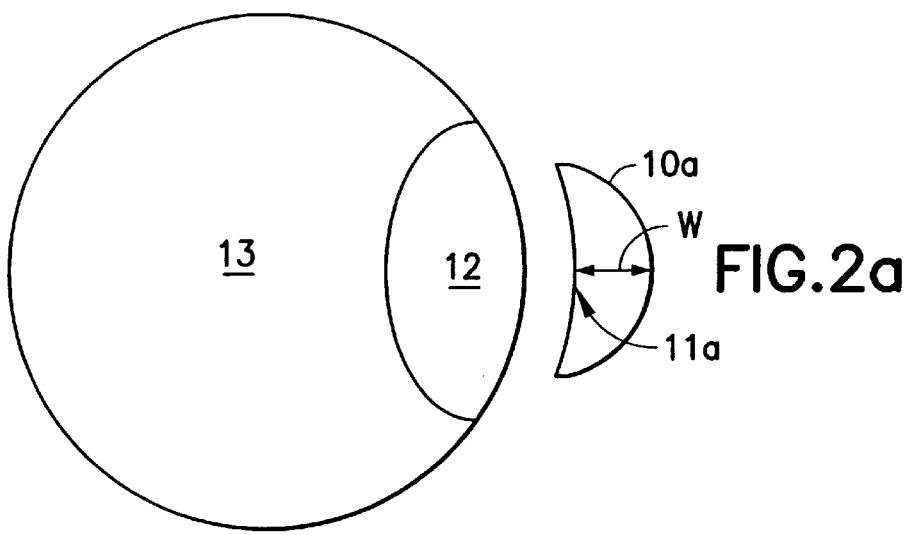
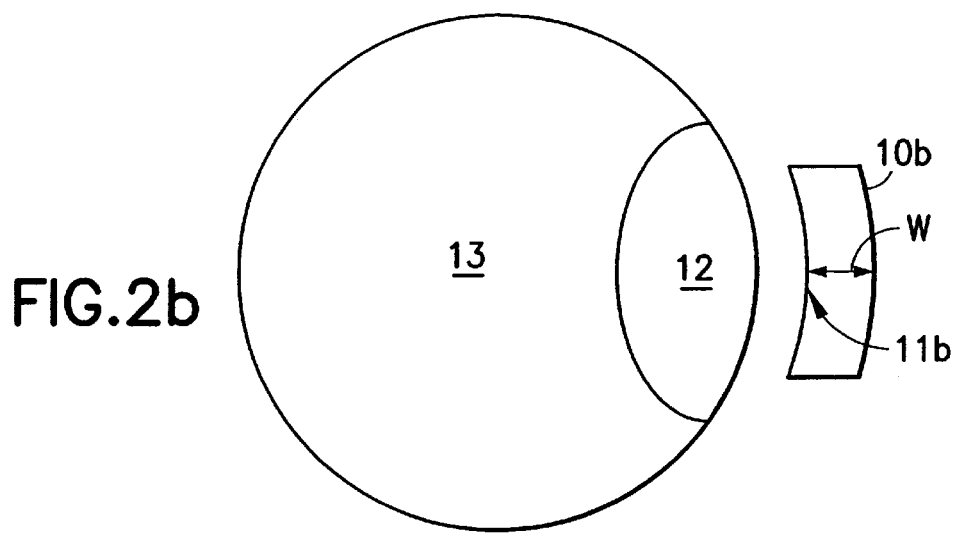
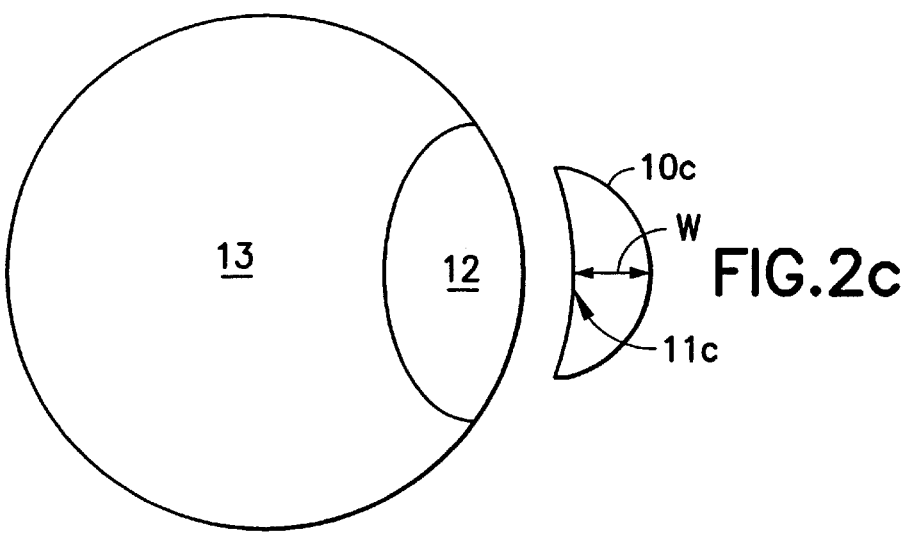

SUPER VISION

FIELD OF THE INVENTION

The present invention relates to vision correction devices and surgical methods and particularly to devices and methods utilized in achieving better than normal vision.

BACKGROUND OF THE INVENTION

For a limited set of individuals, whose occupations entail a high degree of visual acuity, such as fighter pilots, surgeons, certain athletes toolmakers, jewelry workers, etc., achieving emmetropia through spectacles, contact lenses and refractive surgery is vital. Assuming that the myopia, hyperopia and regular astigmatism, if one or more exist, can be eliminated by such conventional means, and the eye achieves emmetropia, BCVA (best corrected visual acuity) can however be degraded by pathological factors such as macular degeneration, a cataract, corneal disease or injury, keratoconus, or irregular astigmatism. Even without these factors, the best value of BCVA in a healthy eye may still only be 20/20. Nevertheless, some individuals achieve 20/15 and some special and unusual individuals may achieve a BCVA value as good as 20/08.

Limitation of visual acuity frequently results from the deviation of the human eye from an ideal optical shape resulting in "spherical aberrations". Those individuals having a vision system with especially low levels of spherical aberration, are the ones with the most acute vision. There is however currently no available technology capable of effectively enhancing the normal degree of best corrected or emmetropic visual acuity, achievable with spectacles, contact lenses and refractive vision surgery, such as by reducing spherical aberrations, to provide a "super" vision for the individuals, such as those described above, who are highly dependent on visual acuity.

SUMMARY OF THE INVENTION

It is accordingly an object of the present invention to provide a method and device, i.e., lens, for achieving enhanced visual acuity.

It is a further object of the present invention to provide such enhanced visual acuity by means of correction for the natural spherical aberration of an eye.

It is yet another object of the present invention to provide a means for subjectively accurately determining the extent of the spherical aberration and a prescription or specification whereby an appropriate correction can be effected.

It is still yet another object of the present invention to provide a test kit geared to provide a subjective evaluation of increase in visual acuity.

Generally the present invention comprises a method and device for achieving enhanced visual acuity for a human eye by the correction of the naturally inherent spherical aberrations therein, which limit visual acuity, beyond what can be achieved by normal refractive corrections.

It has been discovered that spherical aberrations in the imaging system cause a diffusion of focussing along a vision axis which results in a degradation of vision acuity or sharpness of image. In accordance with the present invention, the correction of spherical aberrations in the imaging system of an eye of a patient may be temporarily effected by means of accurate and essentially non-movable placement on the apex of the cornea (i.e., centered on the vision axis) of a selected circularly symmetric test "lens" of uniform thickness, on and near its axial region. The non-refractive axial portion of the test "lens" is aligned with the patient's corneal vision axis. The test "lens" is non refractive (the term "lens" normally refers to a transparent optical element with refractive power but is used loosely herein with reference to transparent, non-refractive devices of varying aspheric shapes) but of pre-determined aspheric shape with respect to the corneal apex. Alternatively, a permanent reduction of spherical aberration may be effected by surgical re-shaping of the cornea to emulate the non refractive, aspheric shape.

Determination of an ideal aspheric "lens" shape is subjectively determined by utilization of a kit of such test "lenses" with varying circularly symmetric, aspheric shapes which are sequentially placed on a patient's cornea until an optimized "lens" shape is subjectively determined. An actual contact lens (hard or soft) is provided to the patient for normal use after the examination, or the patient's eye is surgically reshaped by known means (e.g., with scalpel, excimer laser, water-jet, etc.) to emulate the determined correction in the anterior shape of the corneal tissue. Because of deviations between the corneal vision axis and the axis of the lens, eye glass (spectacle) type corrections are not however feasible unless some means are used to fix the cornea relative to the spectacle lens.

These and other objects, features and advantages of the present invention will become more evident from the following discussion and drawings in which:

SHORT DESCRIPTION OF THE DRAWINGS

Figure 1B:
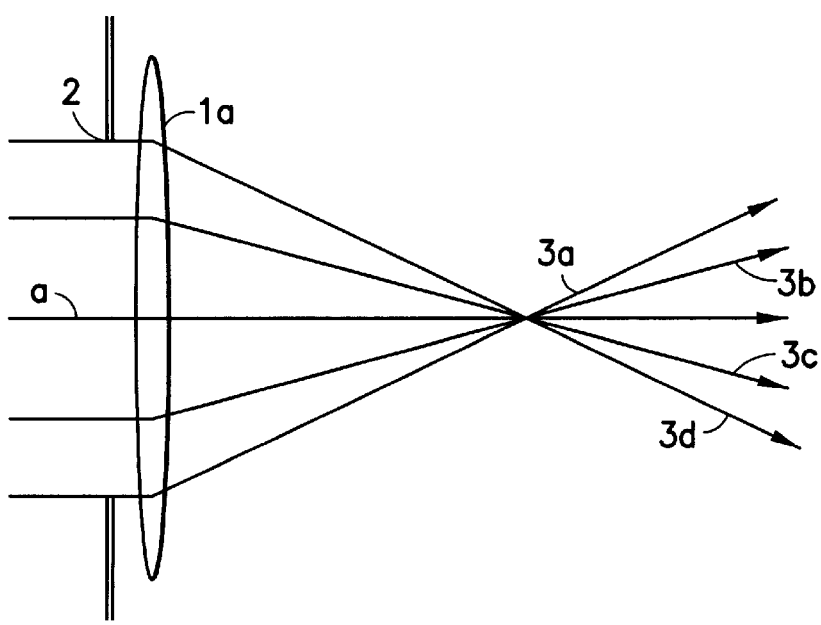
Figure 1B:

FIGS. 1a and 1b depict focussing on an object, with and without presence of spherical aberrations in lenses, respectively, relative to a centered viewing axis.

FIGS. 1a' and 1b' are depictions of image focussing of the lenses of FIGS. 1a and 1b respectively.

FIGS. 2a–c depict eyes being test fitted with various non-refractive lenses of a spherical aberration corrective shape with indication of the correction being effected, and which are part of a series of non-refractive corneal "lenses" of varying aspheric curvatures in a test kit for correction of differing spherical aberrations.

DETAILED DESCRIPTION OF THE INVENTION

In the initial determination of the appropriate corrections in accordance with the present invention, it is understood that there are two parameters which limit optical performance in an optical system: 1) the quality of the optics, and 2) the aperture of the system which admits the light rays.

The ultimate capability of the optics of a system is a condition known as "diffraction-limited". This means that the optical surfaces of the lens system have a perfect aspheric shape and that all light rays of a given wavelength go to the same image point with the ultimate limitation in the minimum size of the point being defined by diffraction of light of the specific wavelength. Light of other wavelengths may focus to a point at a different position along the axis, but that is a different limitation known as chromatic aberration. Astronomical and spy satellite telescopes, photolithographic imaging systems for making silicon integrated circuits, and high magnification microscopes are necessarily diffraction-limited and color corrected because of the high-resolution requirement. In these systems where the optical elements are synthesized it is a relatively straightforward matter to design and manufacture the appropriate optics within the limitations of economics (the Hubble telescope notwithstanding).

However, human eyes form naturally, with imperfect shapes, and retrofitting corrections are instead required. These corrections have nearly always involved refractive corrections. Ideally for ultimate "supervision" capability an eye would have to be conformed to be "diffraction-limited". However refractive changes, common in vision correction devices and surgical procedures (i.e., spectacles, contact lenses and surgery), have no effect relative to such conformation to diffraction limited performance.

If the lens system is diffraction-limited (or is made diffraction-limited), the greater the diameter of the lens aperture, or equivalently, the greater the angular aperture (maximum angle of the bundle of rays passing through the system to a focused spot) the smaller the focused spot and the greater the resolution. However, in many lens systems, the optical system is not diffraction-limited and increasing the aperture may not increase the resolution (while reducing the depth of field). This is precisely the case for the imaging system of the human eye for pupil sizes above a diameter of about 2.5 mm.

The most common source of deviation from diffraction-limited performance in conventional imaging systems is spherical aberration. This imaging defect is apparently inherent in human eyes. To understand spherical aberration, it is useful to first consider the ideal imaging system and then deviations from the ideal, particularly when applied to the human eye.

In optical systems with lens materials having a uniform index of refraction, focusing is achieved by surface shape variation. Typically the index of refraction varies with wavelength, hence, different component lenses of a multi-lens optical system may utilize optical materials of different indices of refraction and different variation with wavelength for color correction. There are also lens components in which the index of refraction varies internally from point to point rather than by altering the surface shape. These latter lenses are designated or called graded-index lenses, with the crystalline lens of the eye being an example of a graded-index lens and the cornea being an example of a uniform index lens.

An ideal diffraction-limited lens has one or more surfaces and each surface is aspheric. In order to calculate the degree of spherical aberration, the following example is provided for a single surface.

A diffraction-limited lens has one or more surfaces and each surface is aspheric in the form of a parabola. The following illustrates the spherical surface and the parabola.

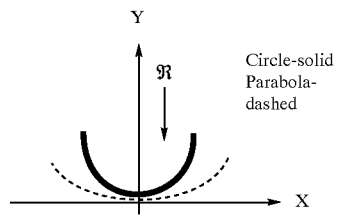
Circle-solid
Parabola-dashed

The equation of the circle of radius, $\Re$, is given by $$\boxed{½ X^2/\Re} + \boxed{X^4/8\Re^3 + X^6/16\Re^5} \longleftarrow \text{Spherical aberration}$$
$$\underbrace{\phantom{XXXXXXXXXXXXXXXXXXXXXXX}}_{\text{Parabola (aspherical)}}$$

The first box/term of the third line represents the ideal parabolic (aspheric) surface of a single surface lens without spherical aberration. The first term in the second dashed box represents the source of the first order spherical aberration in the lens with a spherical surface. The second term represents the order of the error made in considering only the first term, and is the source of higher order spherical aberration. In order to correct to first order for spherical aberration, the surface deviation needs to be corrected by an amount $X^4/8\Re^3$. For the cornea, $\Re \approx 7.8$ mm, and the largest value of X of interest is X=3.5 mm. The maximum amount of correction for first spherical aberration is 40 microns. The maximum higher order error is 4 microns.

The other sources of refractive power are the interface of the posterior surface of the cornea and the aqueous humor, which has a refractive power of −5.8 D and the crystalline lens which has a normal refractive power of about +18 D. These are both small compared to the refractive power of the anterior surface of the cornea. The ideal aspheric system would therefore have to correct for spherical aberration in these components as well. Although a perfect correction would not be feasible, the anterior surface of the cornea can be corrected to partially compensate for these other components with removal of most of the spherical aberration. This would almost triple the resolving power of the eye when the pupil is open to its maximum extent, i.e., diffraction-limited performance out to an aperture radius of 3.5 mm rather than 1.25 mm, which is the current performance.

As a first step in the present invention, it is necessary that the extent of the inherent spherical aberration of a given human eye be initially accurately determined. A subjectively accurate method for determining a proper correction, similar to the current technique for determining refractive error, is one wherein a patient provides feedback regarding the effect of a series of test corrections.

In this regard, in determining what correction should be applied to the anterior cornea surface to minimize spherical aberration in the total lens system of the eye, a patient is first positioned in front of a refractometer. Whatever refractive correction is necessary to achieve emmetropia is first applied with a test refractive lens as is common in determining the refractive prescription. Thereafter, with emmetropia having been established, in accordance with the present invention, a special test contact lens, one of a set, fabricated according to the present invention (such test lenses, without refraction capability, are not otherwise available), with specific aspheric dimensional parameters, is fixedly aligned and placed on the apex of the cornea being measured. Each of the contact lenses in the set is adapted to have no refractive power (i.e., with a uniform thickness near the axis). This is in contrast with the series of lenses used initially to achieve emmetropia wherein the test lens does have refractive power and wherein position fixing is not a critical factor. The aberration correcting contact lens preferably comprises a spherical inside surface for making good contact to the cornea without a gap between the cornea and the test lens. A device such as a lid speculum or scleral chuck is preferably attached to the contact lens to help to locate it precisely on the apex of the cornea (this is based on the assumption that the vision axis extends from such apex) and to fix it in position. The outside surface of the test contact lens is aspheric and has the same curvature on axis as the inside surface, thereby assuring that the test lens has no refractive power along such axis. A series of test contact lenses with different degrees of asphericity are placed on the cornea. The patient is asked to comment on which test lens gives the best subjective visual acuity. This test is similar to what is done during a refraction correction measurement wherein the patient comments on the best test lens for sharpest imaging of a standard Snellen eye chart (but with the differences noted and with the caveat that lenses other than a contact lens type not being readily utilizable for this test).

The best test lens also defines the prescription for refractive correction. Once a particular asphericity is ascertained, that really does improve BCVA, the parameters of the asphericity that should be sculpted onto the cornea are determined. These parameters become part of the specifications or prescription for the refractive correction, if any, and they may be used even when refractive correction is not required. They also might be used in general to improve the baseline from which refractive surgery degrades vision. As a result, a better overall surgical result might be achieved, improving the desirability of having the refractive surgery procedure by providing the ready correction of degradation occurring with such procedures.

Although a hard test lens is preferred it is not absolutely required and a soft lens may be used for both the test lens and actual temporary lens. If a more permanent "super" vision correction is desired, the determined parabolic correction is applied to the cornea with the cornea being reshaped with known methods such as with a scalpel, an excimer laser, water-jet, micro-keratome and the like, in a manner similar to refractive vision corrections but without refractive changes except to the extent necessary to achieve emmetropia.

DETAILED DESCRIPTION OF THE DRAWINGS AND THE PREFERRED EMBODIMENT

With reference to the drawings, in FIGS. 1a and 1b two lenses 1a and 1b respectively, with and without spherical aberrations respectively, are compared with reference to the viewing of an image through identically sized aperture 2. The image is viewed as focussed on central viewing axis "a" with ray paths 3a–d and 3a'–d' respectively. FIG. 1a' is a negative image of best focused bright spot with the optical system of FIG. 1a, containing spherical aberration. In FIG. 1a, various rays 3a–d converge to a focus at different points along the axis "a". The position of focus along the axis depends on the distance of the ray from the axis of the lens as the ray passes through the lens 1a. The lens does not have the required aspheric shape, hence not all rays focus at the same point along the axis. The greater the difference from the ideal aspheric shape, the greater the spread of the distribution of the position of focal points along the axis, hence, the greater the fuzziness of the focused spot observed in the plane at the center of the distribution as seen in FIG. 1a'.

As seen in FIG. 1b, wherein lens 1b is free of spherical aberrations, all rays 3a'–d' converge at a single point on axis "a". Accordingly, as seen in FIG. 1b', a single focused spot is observed in a plane of best focus of a diffraction-limited lens. Only a sharply defined dark spot 5 is produced since all rays focus to the same point along the axis. The diameter of the dark spot is limited by diffraction. The greater the convergence angle of the extreme rays such as 3a' and 3d',i.e., the larger the aperture, the smaller the focused spot size.

In FIGS. 2a–c, a series of aspheric non refractive lenses 10a–c are shown with each having a curved interior 11a–c respectively for fitment onto a cornea 12 of eye, with uniform, non-refractive axial thickness W and with aspheric outer shapes 30a–c corresponding to various corrections over a range for correction of spherical aberrations in eye. The respective lenses 10a–c are successively placed on the cornea 12 of eye 13 and exactly centered and fixed into position thereon until the patient indicates a specific test lens with the greatest subjective degree of enhanced visual acuity being obtained. (It is understood that the controlling factor is the vision axis which normally coincides with the apex of the cornea and not the corneal apex per se.).

FIGS. 2a–c illustrate the three major aberration corrections (those requiring changes to parabolic shape, those requiring changes away from parabolic shape, and those in which correction is required for smaller radius of curvature).

In FIG. 2a, the test lens 10a has the same inner and outer curvatures on the vision axis and therefore has no refractive power. Lens 10a alters the corneal surface shape towards parabolic. In FIG. 2b the test lens 10b has the same inner and outer curvatures on the vision axis and alters the overall shape of the corneal surface away from parabolic. In FIG. 2c the test lens is corrective for a globe with a smaller radius of curvature. Additional, test lenses for refinement of the vision correction will generally fall between the structural parameters of lenses 10a –c.

The radius of curvature of the test lens inside surface should approximately match the radius of curvature of the anterior cornea surface. Therefore, there would be different test lenses for different sizes of eyes. However, the range is not great since contact lenses would otherwise have problems in utilization, yet commercial contact lenses are not specified in this respect. The radius of curvature on axis of the external surface of the test lens should be the same as for its inside surface. This assures the same refractive power for axial rays. Away from the axis, the curvature deviates from that associated with a sphere in order to provide different amounts of spherical aberration. The right amount will compensate for the existing spherical aberration.

It is understood that the above description and example is exemplary of the present invention and that other shapes, structures, and methods are possible without departing from the scope of the present invention as defined in the following claims.

What is claimed is:

1. A method for achieving enhanced visual acuity for a human eye by adapting said eye to correct naturally occurring spherical aberrations therein, said method comprising:
   successively fitting the cornea of the eye with a series of aspheric, non-refractive test lenses of varying aspherical dimensions and shapes; and
   determining the test lens with aspherical dimensions thereof which provides the optimal correction of visual acuity.

2. The method of claim 1 wherein said determination is made subjectively by a patient whose eye is being adapted.

3. The method of claim 1 wherein each said test lens is provided with a non-refractive axial portion substantially positioned and aligned with a corneal vision axis of said eye.

4. The method of claim 3 wherein each said test lens is substantially fixedly positioned and aligned with said vision axis upon said eye.

5. The method of claim 4 wherein said test lenses are provided with a lid speculum or scleral chuck to facilitate positioning and aligning said lens upon said eye in a precise manner.

6. The method of claim 1 which further comprises preparing a wearable contact lens for said eye, said lens configured with the dimensions obtained in said determining step.

7. The method of claim 1 which further comprises reshaping an anterior surface of said cornea to conform to the optimal aspherical dimensions obtained during said determining step.

8. The method of claim 7 wherein said anterior surface is reshaped with surgical means adapted for conforming said surface with said optimal dimensions.

9. The method of claim 8 wherein said surgical means is a scalpel, a laser or a water jet.

10. The method of claim 1 wherein said eye is additionally corrected for refractive vision correction, in addition to the correction of said spherical aberration.

11. An aspheric lens for correcting naturally occurring spherical aberrations in a human eye, said lens configured and adapted to be substantially fixedly positioned and aligned with the corneal vision axis of said eye in accordance with the method of claim 4.

12. The aspheric lens of claim 11 wherein said lens is non-refractive relative to an apex of said cornea.

13. The aspheric lens of claim 11 wherein said lens is non-refractive relative to a vision axis through said cornea.

14. A wearable contact lens made in accordance with the method of claim 6.

15. A method of achieving enhanced visual acuity for a human eye by adapting said eye to correct naturally occurring spherical aberrations therein, said method comprising:
   successively fitting the cornea of the eye with a series of aspheric, non-refractive test lenses of varying aspherical dimensions and shapes;
   determining the test lens with aspherical dimensions thereof which provides the optimal enhancement of visual acuity; and
   preparing a wearable contact lens for said eye, said lens configured with the dimensions obtained in said determining step.

16. A method of achieving enhanced visual acuity for a human eye by adapting said eye to correct naturally occurring spherical aberrations therein, said method comprising:
   successively fitting the cornea of the eye with a series of aspheric, non-refractive test lenses of varying aspherical dimensions and shapes;
   determining the test lens with aspherical dimensions thereof which provides the optimal enhancement of visual acuity; and
   reshaping an anterior surface of said cornea with surgical means adapted for conforming said surface with said optimal dimensions.

17. The method of claim 16 wherein said surgical means is a scalpel, a laser or a water jet.

* * * * *